United States Patent
Tuliakov et al.

(10) Patent No.: US 9,427,174 B2
(45) Date of Patent: Aug. 30, 2016

(54) ENDOSCOPE APPARATUS AND CONTROL METHOD FOR ADJUSTING LIGHT BEAM BASED ON GEOMETRY OF BODY

(71) Applicant: SAMSUNG ELECTRONICS CO., LTD., Suwon-si (KR)

(72) Inventors: Stepan Tuliakov, Suwon-si (KR); Tae-hee Lee, Seoul (KR); Seung-ki Cho, Suwon-si (KR); Hee-chul Han, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 337 days.

(21) Appl. No.: 13/973,351

(22) Filed: Aug. 22, 2013

(65) Prior Publication Data

US 2014/0228635 A1 Aug. 14, 2014

(30) Foreign Application Priority Data

Feb. 14, 2013 (KR) .................. 10-2013-0015969

(51) Int. Cl.
*A61B 1/06* (2006.01)
*A61B 5/107* (2006.01)
*A61B 1/00* (2006.01)

(52) U.S. Cl.
CPC ......... *A61B 5/1076* (2013.01); *A61B 1/00009* (2013.01); *A61B 1/06* (2013.01); *A61B 1/0607* (2013.01); *A61B 1/0684* (2013.01)

(58) Field of Classification Search
CPC .... A61B 1/0623; A61B 1/06; A61B 1/0684; A61B 5/1076; A61B 5/1079
USPC .................. 600/167, 168, 173, 178, 180
See application file for complete search history.

(56) References Cited

U.S. PATENT DOCUMENTS

| | | | | |
|---|---|---|---|---|
| 1,740,229 A | * | 12/1929 | Dorey ................... | F21S 8/00 362/243 |
| 4,678,900 A | * | 7/1987 | Nishioka ................ | A61B 1/05 250/205 |
| 4,706,657 A | * | 11/1987 | Miyagi ................ | A61B 1/0669 600/178 |
| 5,473,373 A | * | 12/1995 | Hwung ................ | H04N 5/202 348/254 |
| 5,749,830 A | | 5/1998 | Kaneko et al. | |
| 6,078,686 A | * | 6/2000 | Kim ..................... | H04N 1/58 348/E9.042 |

(Continued)

FOREIGN PATENT DOCUMENTS

CN 1443510 A 9/2003
CN 102753079 A 10/2012

(Continued)

OTHER PUBLICATIONS

Communication from the European Patent Office issued Apr. 3, 2014 in a counterpart European Application No. 14150815.0.

(Continued)

*Primary Examiner* — John P Leubecker
(74) *Attorney, Agent, or Firm* — Sughrue Mion, PLLC

(57) ABSTRACT

An endoscopic apparatus is disclosed. The endoscopic apparatus includes a light source which has a plurality of light source components which output light beams which cross one another; an estimator which estimates a geometry of an internal surface of a body; and a controller which controls so that an intensity of a light beam output by any one of the plurality of light source components is variably adjusted based on the estimated geometry of the internal surface of the body.

19 Claims, 12 Drawing Sheets

(56) References Cited

U.S. PATENT DOCUMENTS

| | | |
|---|---|---|
| 6,918,872 B2 | 7/2005 | Yokoi et al. |
| 7,452,328 B2 * | 11/2008 | Homan ................ A61B 1/041 600/101 |
| 8,477,183 B2 | 7/2013 | Koizumi et al. |
| 2003/0171652 A1 | 9/2003 | Yokoi et al. |
| 2003/0171653 A1 | 9/2003 | Yokoi et al. |
| 2006/0183976 A1* | 8/2006 | Adler ................ A61B 1/00096 600/176 |
| 2007/0038030 A1* | 2/2007 | Kaneko ............ A61B 1/00096 600/180 |
| 2007/0039077 A1* | 2/2007 | Takami .............. A61B 1/0638 600/180 |
| 2009/0306474 A1* | 12/2009 | Wilson ................ A61B 1/041 600/109 |
| 2012/0041267 A1* | 2/2012 | Benning ............ A61B 1/0607 600/180 |
| 2012/0078046 A1 | 3/2012 | Sasaki et al. |
| 2012/0134155 A1* | 5/2012 | Wendt ..................... F21S 2/00 362/249.03 |
| 2012/0242812 A1 | 9/2012 | Koizumi et al. |
| 2012/0302893 A1 | 11/2012 | Ishihara |
| 2014/0055585 A1* | 2/2014 | Akiyama ........... G02B 23/2423 348/68 |

FOREIGN PATENT DOCUMENTS

| | | |
|---|---|---|
| CN | 102869297 A | 1/2013 |
| EP | 2 547 093 A1 | 1/2013 |

OTHER PUBLICATIONS

Communication dated Jun. 7, 2016, issued by the State Intellectual Property Office of P.R. China in counterpart Chinese Application No. 201410051099.8.

* cited by examiner

ENDOSCOPE APPARATUS AND CONTROL METHOD FOR ADJUSTING LIGHT BEAM BASED ON GEOMETRY OF BODY

CROSS-REFERENCE TO RELATED APPLICATIONS

This application claims priority from Korean Patent Application No. 10-2013-0015969, filed in the Korean Intellectual Property Office on Feb. 14, 2013, the disclosure of which is incorporated herein by reference in its entirety.

BACKGROUND

1. Field

Methods and apparatuses consistent with exemplary embodiments relate to an endoscopic apparatus and control method thereof, and more particularly to an endoscopic apparatus which uses a plurality of light sources and a control method thereof.

2. Description of the Related Art

An endoscopic apparatus is an apparatus which may be used for photographing and observing a narrow space, such as an inside portion of a human body or machine. In particular, an endoscopic apparatus in the medical field enables a user to observe an interior portion of a human body (e.g., stomach, bronchial tubes, throat, large intestine, small intestine, and/or any other internal organ or portion) by using a small camera, and to check the condition thereof without having to cut the abdomen open or make an incision.

Existing endoscopic apparatuses are being increasingly used for various industrial purposes, such as enabling a user to observe an interior portion of a precision machine without having to dissolve the precision machine, enabling a user to check the condition inside a pipe, and/or other similar types of purposes.

A general endoscopic apparatus is equipped with a miniature camera and a light source at a front end of a bending apparatus which is configured for obtaining images, and inside the bending apparatus there is provided an adjusting wire which is configured for adjusting a bending of the bending apparatus. The adjusting wire is typically embedded inside a long and narrow insertion tube and connected to a handle which has an up/down left/right activator which is configured for adjusting respective bending directions. The insertion tube is formed to have a predetermined length so as to reach inside a human body or precision machine.

FIGS. 1A, 1B, and 1C are views which illustrate respective shortcomings of a conventional endoscopic apparatus of related art.

As illustrated in FIG. 1A, an endoscopic apparatus of related art provides different amounts of light to different areas on an internal surface of a human body, and thus there is a problem that it may be difficult to obtain clear images, as illustrated, for example, in dark areas as indicated in circles in FIG. 1B and FIG. 1C, or in highlighted areas such as that indicated in the left circle in FIG. 1C.

SUMMARY

The purpose of the exemplary embodiments is to provide an endoscopic apparatus which provides illumination based on a geometry of an internal surface of a body and a control method thereof.

According to an exemplary embodiment, an endoscopic apparatus includes a light source which includes a plurality of light source components which are configured to output light beams which cross one another; an estimator which is configured to estimate a geometry of an internal surface of a body; and a controller which is configured to control so that an intensity of a light beam output by any one of the plurality of light source components is variably adjusted based on the estimated geometry of the internal surface of the body.

In addition, the endoscopic apparatus may further include a light adjuster which is configured to adjust an output state of at least one of a plurality of light beams output by the plurality of light source components, and the controller may be further configured to control the light adjuster to adjust at least one of an emission direction and emission extent of at least one of the plurality of light beams based on the estimated geometry of the internal surface of the body.

In addition, the endoscopic apparatus may further include a photographer which is configured to photograph the internal surface of the body, and the estimator may be further configured to estimate the geometry of an internal surface of the body based on an image which is generated by the photographer.

In addition, the endoscopic apparatus may further include a depth sensor which is configured to sense a depth of the internal surface of the body, and the estimator may be further configured to estimate the geometry of the internal surface of the body based on the depth sensed by the depth sensor.

In addition, the controller may be further configured to adjust an intensity of at least one of the plurality of light beams based on an angle between a normal component with respect to the estimated geometry of the internal surface of the body and a direction of the at least one of the plurality of light beams.

According to an exemplary embodiment, an endoscopic method may include estimating a geometry of an internal surface of a body; and variably adjusting an intensity of a light beam which is output by one of a plurality of light source components based on the estimated geometry of the internal surface of the body, and the plurality of light source components are configured to output a respective plurality of light beams which cross one another.

In addition, the endoscopic method may further include adjusting an output state of at least one of the plurality of light beams output by the plurality of light source components, and the adjusting the output state of the at least one of the plurality of light beams may include variably adjusting at least one of an emission direction and emission extent of at least one of the plurality of light beams based on the estimated geometry of the internal surface of the body.

In addition, the endoscopic method may further include photographing the internal surface of the body, and the estimating the geometry of the internal surface of the body may including estimating the geometry of the internal surface of the body based on an image which is obtained as a result of the photographing.

The endoscopic method may further include sensing a depth of the internal surface of the body, and the estimating the geometry of the internal surface of the body may include estimating the geometry of the internal surface of the body based on the sensed depth.

The variably adjusting the intensity of the light beam may include variably adjusting the intensity of the light beam based on at least one of a normal component with respect to the estimated geometry of the internal surface of the body, a direction of the light beam, a distance between the one of the plurality of light source components from which the light beam is output and the internal surface of the body, and a refraction ratio which relates to the internal surface of the body.

According to the aforementioned exemplary embodiments, it becomes possible to provide illumination which dynamically changes based on the geometry of the internal surface of the body.

BRIEF DESCRIPTION OF THE DRAWINGS

The above and/or other aspects will be more apparent by describing certain exemplary embodiments with reference to the accompanying drawings, in which.

DETAILED DESCRIPTION

Certain exemplary embodiments are described in detail below with reference to the accompanying drawings.

Figure 1A:
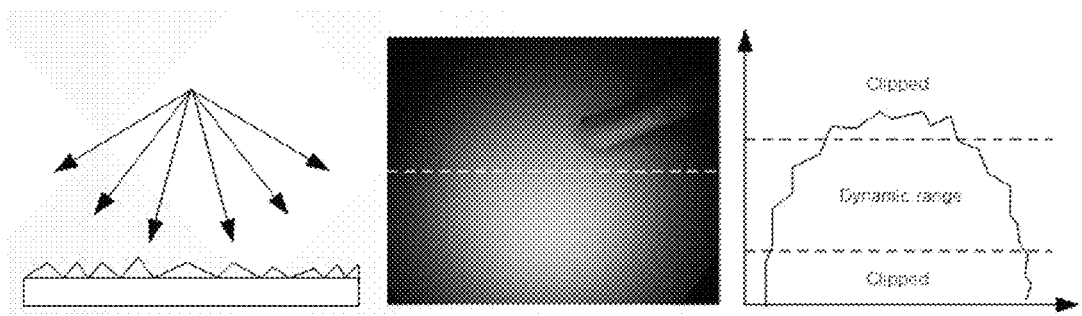
FIGS. 1A, 1B, and 1C are views which illustrate related art.
Figure 1B:
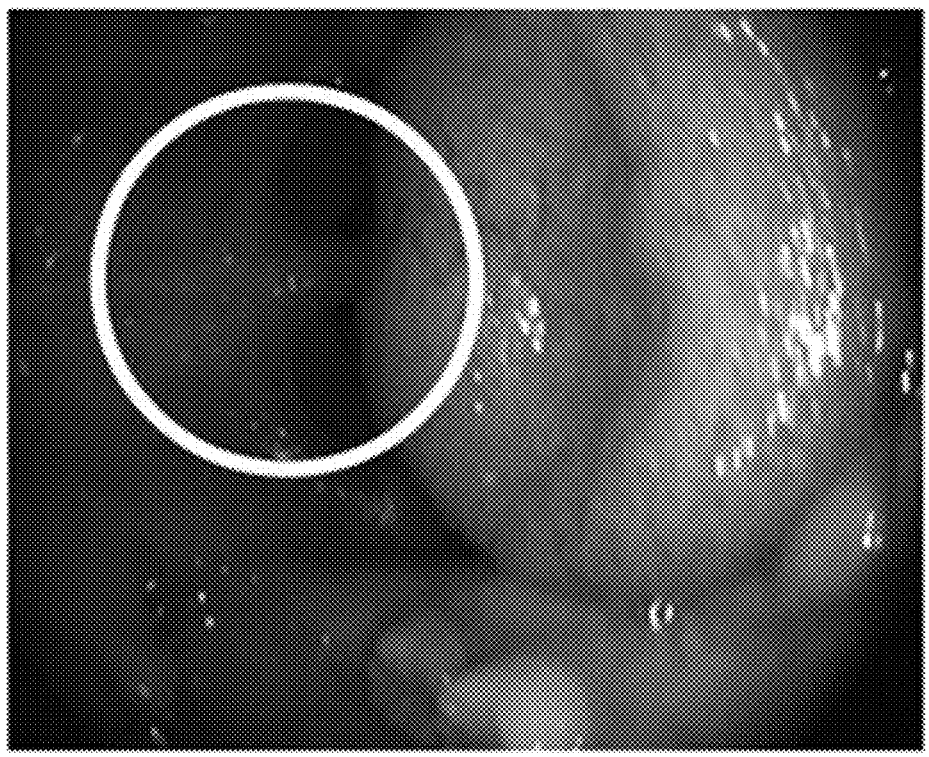
Figure 1C:
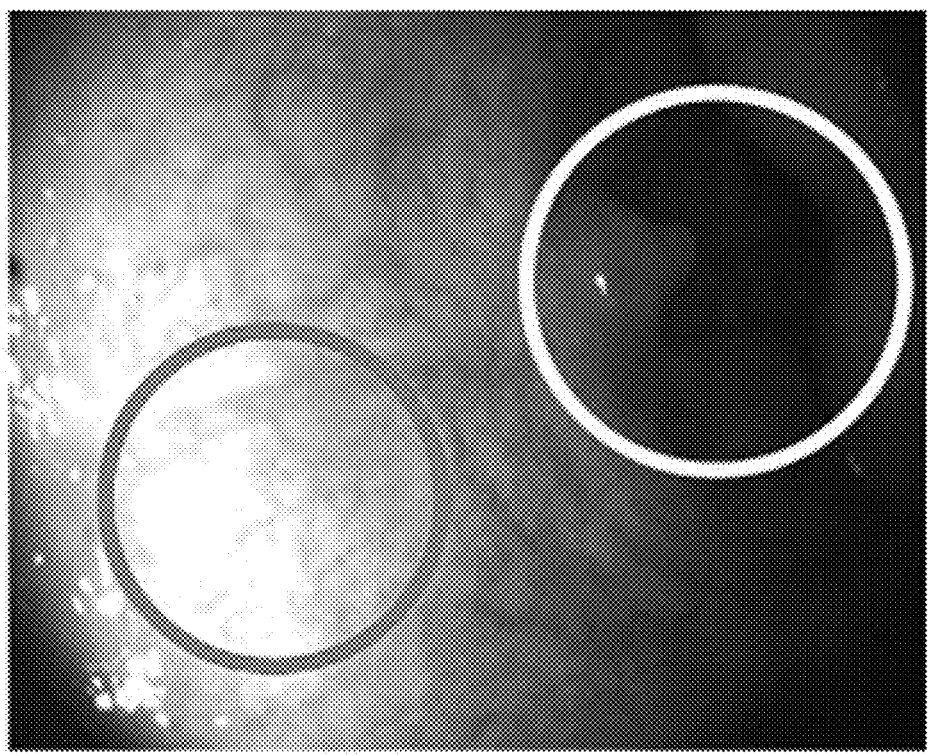
Figure 2A:
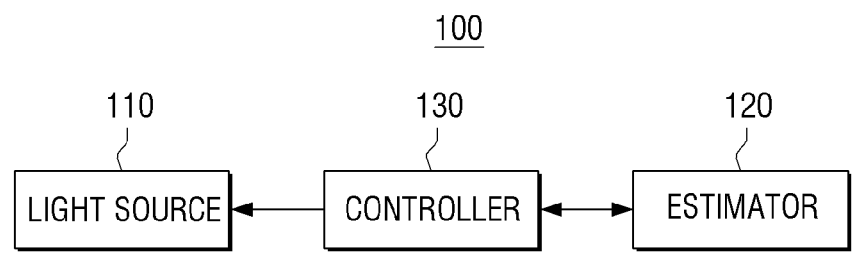
FIGS. 2A and 2B are block diagrams which illustrate configurations of an endoscopic apparatus, according to various exemplary embodiments.
Figure 2B:
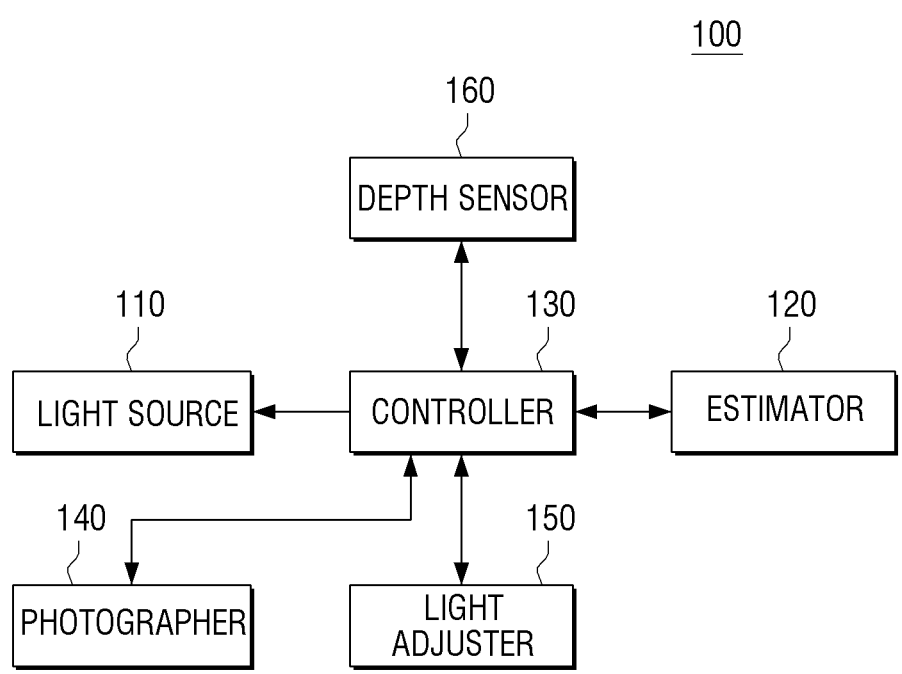

FIGS. 2A and 2B are block diagrams which illustrate configurations of an endoscopic apparatus, in accordance with various exemplary embodiments.

As shown in FIG. 2A, an endoscopic apparatus 100 in accordance with one or more exemplary embodiments includes a light source 110, an estimator 120, and a controller 130.

The light source 110 has a plurality of light source components. In particular, the light source 110 has a plurality of light source components which output light beams of arbitrary shapes which cross one another.

Herein, the light source 110 may be embodied as a light-emitting diode (LED) array, but is not limited thereto. For example, the LED array may be arranged on a circular two-dimensional layout.

According to another exemplary embodiment, it is possible to use a xenon lamp laser diode as a component of the light source 110.

The estimator 120 is configured to estimate a geometry of an internal surface of a human body via any one or more of various methods.

Specifically, the estimator 120 may use a depth sensor, perform intensity distribution analysis, and/or estimate geometry of an internal surface of a human body by performing light probing.

The controller 130 controls overall operations of the endoscopic apparatus 100. The controller 130 may include a CPU (central processing unit), a module for controlling the endoscopic apparatus 100, and/or at least one of a ROM (Read Only Memory) and RAM (Random Access Memory) for storing data.

In particular, the controller 130 may control to adjust an intensity of at least one of a plurality of light beams based on a geometry of an internal surface of a human body. More particularly, the controller 130 may control to adjust the intensity of the at least one of the plurality of light beams so as to provide illumination which is optimized to the geometry of the internal surface of the human body. Herein, the geometry of the internal surface refers to a spatial topography of the internal surface of the human body, including height. The following is a description of a specific method for adjusting an intensity of at least one of a plurality of light beams based on the geometry of the internal surface of the human body.

In addition, the endoscopic apparatus 100 may further include a light delivery member (not illustrated) which is configured to deliver light emitted from the light source 110, thereby illuminating a particular body area inside the body. The light delivery member (not illustrated) may be embodied as a narrow and long insertion unit which is insertable into the body, which insertion unit includes a plurality of optical fiber bundles.

FIG. 2B is a block diagram which illustrates a configuration of an endoscopic apparatus in accordance with another exemplary embodiment. A detailed explanation of the parts which overlap with the configurative elements illustrated in FIG. 2A from among the configurative elements illustrated in FIG. 2B will be omitted.

The photographer 140 is configured to photograph the internal surface of the body. An image photographed by the photographer 140 may be used for an estimation of the geometry of the internal surface of the body by the estimator 120.

In particular, the photographer 140 may photograph the internal surface of the body based on the plurality of light beams provided via the light source 110. To this end, the photographer 140 may include a camera unit which includes a lens and an image sensor, such as, for example, a charge coupled device (CCD).

In an exemplary embodiment, the image which enters the CCD is converted into an electronic signal, transmitted to an image processor, and is then reconverted into an image signal by the image processor (not illustrated), and is then output via a display unit (not illustrated).

The light adjuster 150 adjusts the respective output state of one or more of the plurality of light beams output by the plurality of light source components. Herein, the output state of a particular one of the plurality of light beams may be indicated by at least one of the emission direction of the particular light beam and an emission extent of the particular light beam. Herein, the term "emission extent" refers to the extent of increase of the diameter of the particular light beam. The emission extent may be adjusted by adjusting an emission angle which relates to the corresponding light source component.

In particular, the light adjuster 150 may include a lens (not illustrated) which refracts each of the plurality of light beams in a predetermined direction, a light beam emission angle adjusting lens (not illustrated) which adjusts the emission extent of each of the plurality of light beams, and a filter (not illustrated), such as, for example, an emission angle converter, but which is not limited thereto. For example, the lens may be configured as a lens array which is arranged on a front surface of an LED array.

The light adjuster 150 may variably adjust at least one of the emission direction and the emission extent of at least one of the plurality of light beams which are output by the plurality of light source components based on the estimated geometry of the internal surface of the body, which has been estimated by the estimator 120 based on the control of the controller 130. For example, in a case where the internal surface of the body is relatively high, the light adjuster 150 may adjust the emission angle between at least one of the plurality of light beams output by the plurality of light source components and a normal component with respect to the estimated geometry of the internal surface of the body is small.

A depth sensor 160 is configured for sensing a depth of the internal surface of the body. The depth sensor 160 may be embodied as a depth camera, but provided that the depth sensor 160 is an apparatus which is capable of sensing the depth, it is not limited thereto.

In this case, the estimator 120 may be configured to estimate the geometry of the internal surface of the body based on the depth information sensed by the depth sensor 160.

Figure 3A:
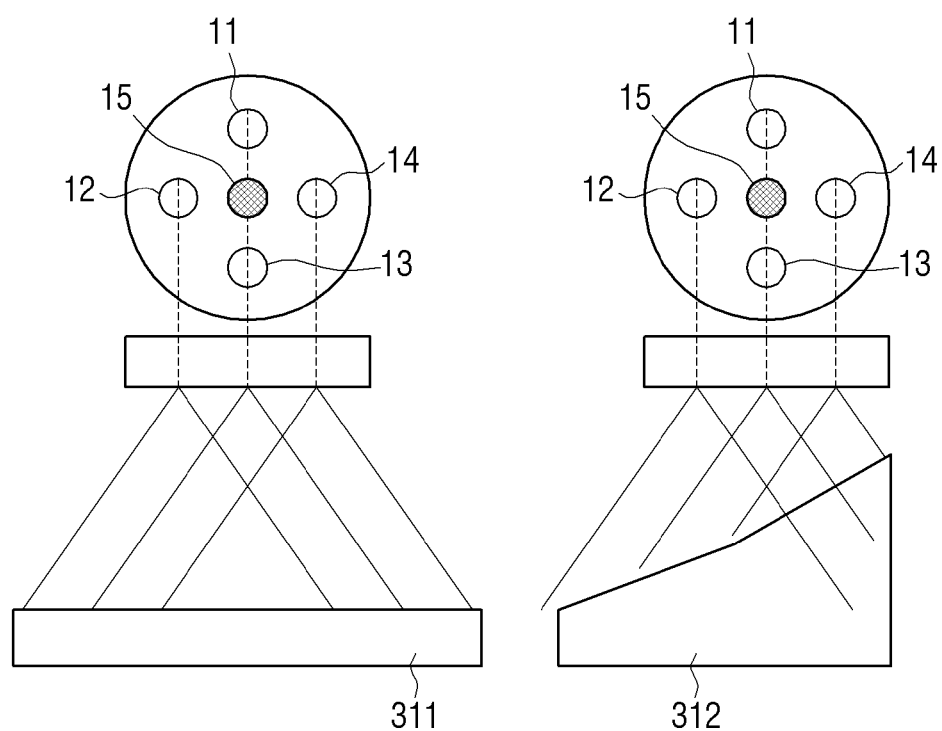
FIGS. 3A, 3B, 3C, and 4 are views which illustrate a method for adjusting an output state of each of a plurality of light beams, in accordance with one or more exemplary embodiments.
Figure 3B:
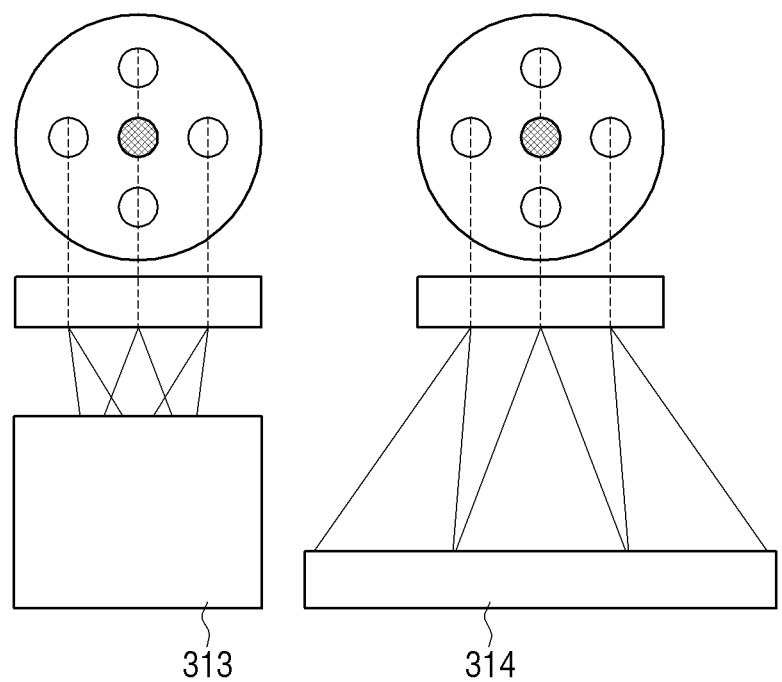
Figure 3C:
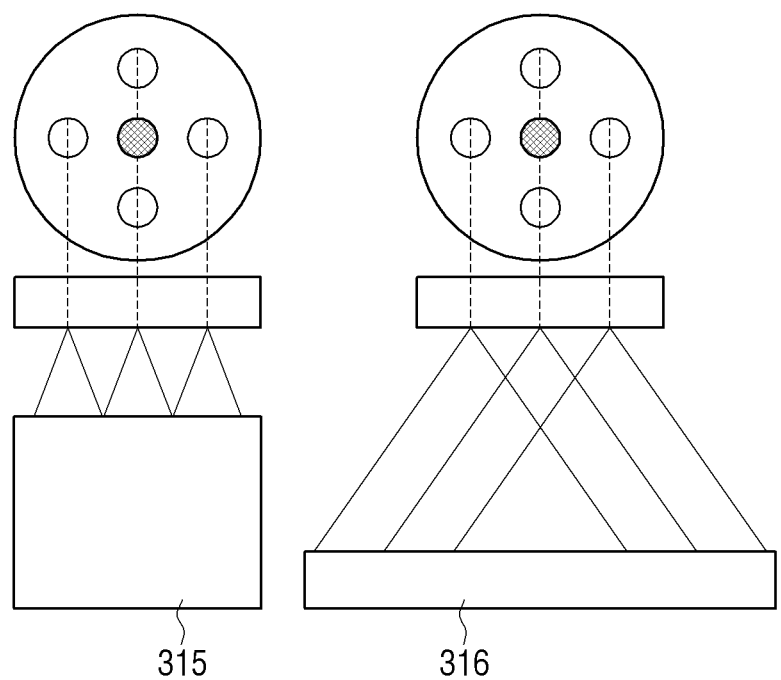

The following is a description of a method for adjusting the output state of at least one of the plurality of light beams by using the controller 130, with reference to FIGS. 3A, 3B, and 3C.

As illustrated in FIG. 3A, it is possible to adjust the extent of each of the plurality of light beams 11, 12, 13, 14, and 15 based on the geometry of the internal surface of the body. For example, it is possible to adjust the intensity of each respective one of the plurality of beams to be uniform in the portion 311 where the height of the internal surface of the body is the same, and to variably adjust the intensity of each respective one of the plurality of beams to be different in the portion 312 where the height of the internal surface of the body is not the same.

In addition, as illustrated in FIG. 3B, it is possible to adjust the emission direction of each of the plurality of light beams based on the geometry of the internal surface of the body. For example, it is possible to adjust the emission direction of each respective one of the plurality of light beams to tend to converge for the area 313 where the surface height is high, and to tend to diverge for the area 314 where the surface height is low.

In addition, as illustrated in FIG. 3C, it is possible to adjust the emission extent of each of the plurality of light beams based on the geometry of the internal surface of the body. For example, it is possible to adjust the emission extent of each respective one of the plurality of light beams by adjusting the emission angle of each of the light beams with respect to a normal to be relatively small in the area 315 where the average surface height is high, and by adjusting the emission angle of each of the light beams with respect to the normal to be relatively large in the area 316 where the average surface height is low.

Further, the controller 130 may control to adjust the extent of each of the plurality of light beams based on at least one of the angle between the direction of the normal component with respect to the internal surface of the body and each of the plurality of light beams, a distance between at least one of the plurality of light source components and the internal surface of the body, and a refraction ratio which relates to the internal surface of the body.

For example, the pixel value of the photographed image $I=[I_1, \ldots, I_N]^T$ may be calculated by applying the mathematical formula below:

$$I = k_d(Ai_0) \quad \text{[Mathematical formula 1]}$$

$$k_d = \begin{bmatrix} k_{d1} & 0 & \cdots & 0 \\ 0 & k_{d2} & 0 & \vdots \\ \vdots & 0 & \ddots & 0 \\ 0 & \cdots & 0 & k_{dX} \end{bmatrix}$$

-continued $$A = \begin{bmatrix} a_{11} & \cdots & a_{1M} \\ \vdots & \ddots & \vdots \\ a_{N1} & \cdots & a_{NM} \end{bmatrix}$$

$$a_{ij} = \cos(\alpha_{ij})/r_{ij}^2$$

Herein, A is the surface geometry matrix, $k_{di}$ is the surface refraction ratio, $\alpha_{ij}$ is the angle between the normal component and the direction of the light beam emitted by light source j, $r_{ij}$ is the distance between i and j, $N=w \times h$ is the number of image pixels, and $i_o=[i_{1o}, \ldots, i_{1M}]^T$ is the irradiance of the light source.

Figure 4:
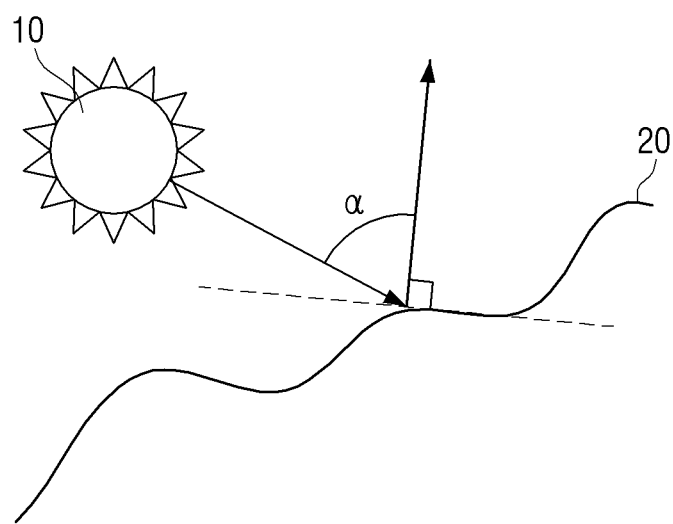

FIG. 4 is a view which illustrates a method for calculating $\alpha_{ij}$ as expressed above in mathematical formula 1.

As illustrated in FIG. 4, $\alpha_{ij}$ may be calculated as the angle between the normal component with respect to the body surface 20 and the direction of the light beam emitted by the light source 10.

In particular, in mathematical formula 1 as expressed above, $Ai_0$ is hereinafter referred to as the scene geometry.

In order to offset the scene geometry $Ai_0$, the light beam emission and the light beam intensity are adjusted by adjusting hardware components, and a illumination compensation may be performed by using software. The method for performing illumination compensation by using software will be described below with reference to FIG. 5.

Further, the optimal intensity of illumination $\hat{i}_o$ may be calculated by applying the following mathematical formula:

$$\hat{i}_0 = \underset{i_0}{\mathrm{argmin}} f(i_0) \quad \text{[Mathematical formula 2]}$$

$$f(i_0) = (Ai_0 - 1)^T (Ai_0 - 1)$$

Herein, $1=[1, \ldots, 1]^T$ is an N*1 vector.

Next, the following mathematical calculation is performed:

$$\partial f/\partial i_0 = \frac{\partial(i_0^T A^T A i_0 - i_0^T A^T - Ai_0 + 1)}{\partial i_0} = 0 \quad \text{[Mathematical formula 3]}$$

$$2A^T A i_0 - 2A^T 1 = 0$$

By applying both of the above mathematical formulas, the following formula for calculating the optimal intensity of illumination $\hat{i}_o$ may be derived:

$$\hat{i}_o = (A^T A)^{-1} A^T 1$$

$$\hat{i}_o' = (\hat{i}_o \cdot k) = (A^T A)^{-1} A^T (1 \cdot k) \quad \text{[Mathematical formula 4]}$$

Further, as additionally described above, it is possible to adjust one or both of the emission and the direction of each of the light beams.

Next, the surface geometry matrix A is estimated in order to facilitate a calculation of the optimal intensity of illumination $\hat{i}_o$.

In this case, it is possible to estimate the surface geometry matrix A by using light source overlap and depth information.

Using the light source overlap and depth information, the following formula is derived:

$$I = k_d(Ai_0) = k_d(A_1 i_{10} + \ldots + A_M i_{M0})$$

$$A=[A_1, \ldots A_M] \quad \text{[Mathematical formula 5]}$$

Accordingly, it is possible to discover $A_1, \ldots, A_M$ as expressed in the following formula, with respect to M images $I_1, \ldots, I_M$ with one light source per image:

$$A_k = \text{Lowpass}(I_k)/i_{k0} \quad \text{[Mathematical formula 6]}$$

However, it is not practical to turn off all light source components completely.

In order to avoid this, it is possible to adjust the intensity of each respective light beam output by each light source component slightly differently as expressed below:

$$I^{(1)} = k_d(A_1 i_{10} + \ldots + A_k i_{k0}^{(1)} + \ldots + A_M i_{M0})$$

$$I^{(2)} = k_d(A_1 i_{10} + \ldots + A_k i_{k0}^{(2)} + \ldots + A_M i_{M0}) \quad \text{[Mathematical formula 7]}$$

Accordingly, the following formula may be derived:

$$A_k = \text{LowPass}(\Delta I_k)/\Delta i_{k0}$$

$$\Delta I = k_d A_k \Delta i_{k0} \quad \text{[Mathematical formula 8]}$$

Herein, searching may be performed by using a sufficient frame rate.

Assuming that the light source illuminates a particular portion of the internal surface of the body such that an image of the particular portion of the body is obtained, and all light is adjusted in accordance with the average intensity of the corresponding image, the formula as expressed below may be derived:

$$i_{01}(t) = i_{01}(t-1) + l(I_{opt} - \bar{I}_{01}(t))$$

$$i_{0M}(t) = i_{0M}(t-1) + l(I_{opt} - \bar{I}_{0M}(t)) \quad \text{[Mathematical formula 9]}$$

$I_{opt}$=optical image intensity

The average intensity of the image area illuminated by $I_{0k}(t)$–optical $i_{0k}(t)$ $i_{0k}(t)$=optical intensity However, all pixels of a normal image are affected by all light source components.

Figure 5:
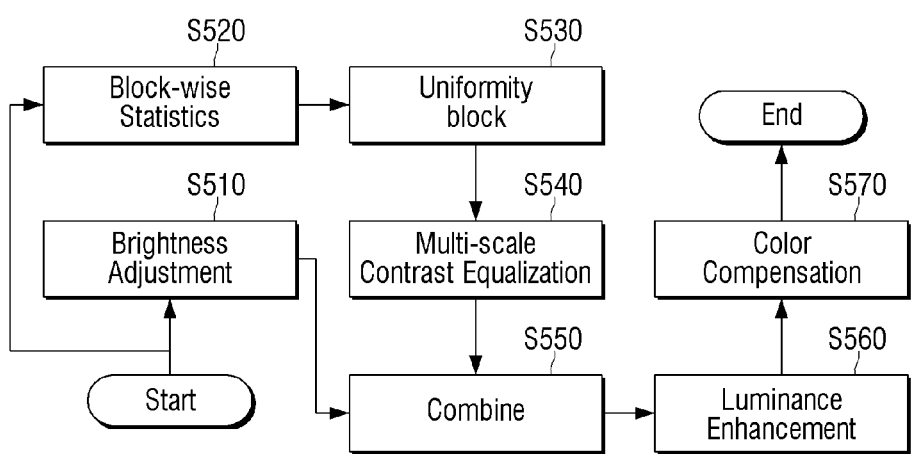
FIGS. 5 and 6 are views which illustrate a software rewarding method, in accordance with one or more exemplary embodiments.

FIG. 5 is a view which illustrates a software algorithm, according to one or more exemplary embodiments.

First, in operation S510, with respect to the input image, a brightness adjustment is performed.

In particular, the overall brightness is adjusted. Brightness adjustment is a static entire mapping of an input fimbriation brightness value Yb (see FIG. 6, drawing (a)). The brightness adjustment increases the contrast and brightness of the relatively dark area, but compresses the relatively bright area. In addition, the brightness adjustment preserves the contrast in a very dark area in order to prevent an increase of noise.

However, the overall brightness adjustment tends to cause a dynamic range loss in the bright area. Thus, it may appear as if the color has faded after the brightness adjustment. In order to overcome this problem, it is possible to perform a local contrast enhancement. A human visual system is more sensitive to a local contrast than to the original contrast. More specifically, the local contrast enhancement method, as applied to the present exemplary embodiment, is based on the CLAHE (Contrast Limited Adaptive Histogram Equalization) method. This local contrast enhancement method employs a new statistics-based approach in order to prevent an increase of noise and contrast defects, and uses the multi-scale CLAHE method in order to improve the contrast in different scales at the same time.

First, a statistics-based approach is introduced in order to prevent an increase of noise and contour defects. CLAHE may generate defects in some image areas, and thus detect the corresponding area, and may use local statistic characteristics to reduce the extent of contrast enhancement in that area.

In addition, an entropy-based parameter is used to detect the processing area having noise or contour defect, and to exclude the detected area. In addition, the entropy-based parameter αH is combined with the average-based control parameter am in order to predetermine the histogram clipping limit C as expressed in the following formula which relates to all block areas:

$$C(i) = C_m + C_n \times \alpha_H(i) \times \alpha_m(i) \quad \text{[Mathematical formula 10]}$$

Herein, Cm is a minimum clipping limit, Cn is a normal clipping limit, and I is an index.

Figure 6:
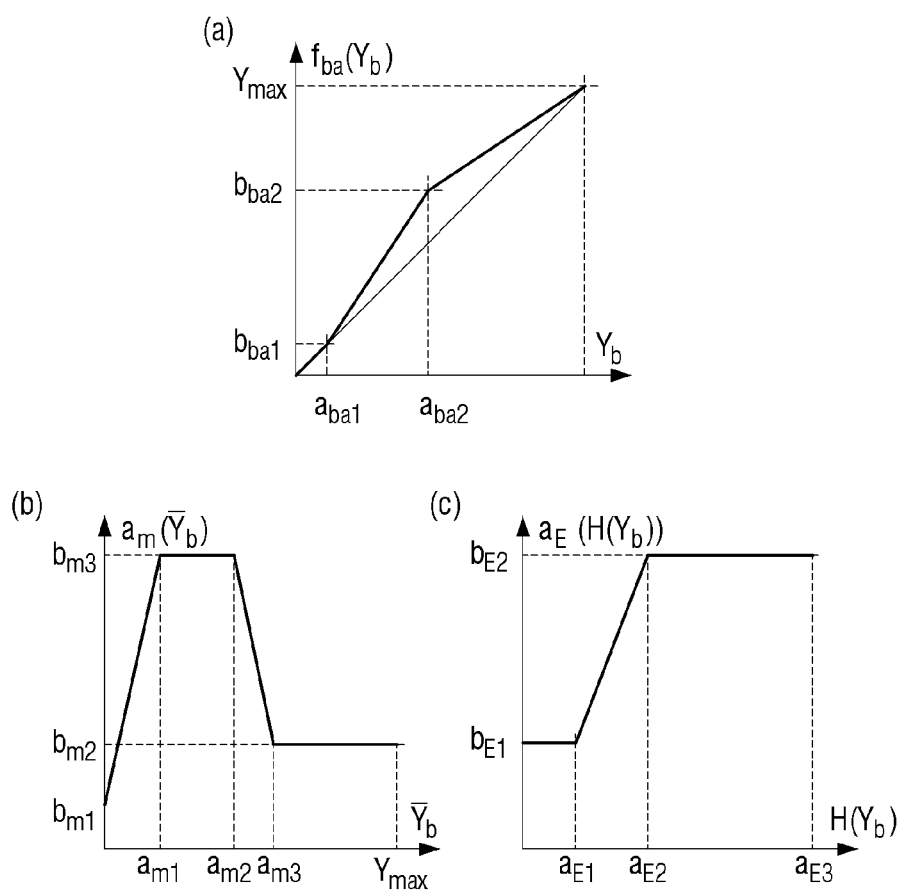

The average-based parameter am improves the local contrast of the middle tone and bright area, while preventing the over-enhancement of the dark area and the brightest area of the image which is compressed by the overall brightness adjustment procedure. αm is subordinated to the average fimbriation brightness of each block $\bar{Y}_b$ (see FIG. 6, drawing (b)).

The entropy-based parameter αH depends on the entropy $H(\bar{Y}_b)$ of the fimbriation brightness histogram of each block (see FIG. 6, drawing (c)). In addition, the entropy-based parameter prevents an increase of contour defects and an increase of noise in the uniform area and in the individual uniform area.

Secondly, the CLAHE-based multi-scale contrast enhancement method is applied. The use of CLAHE improves the contrast of different areas, based on the CLAHE block size. Therefore, the CLAHE results obtained for the blocks of various sizes are combined.

More particularly, as expressed in the following formula, all respective CLAHE results Yces which are obtained for each different block size hs*wa are directly added:

$$Y_{ce} = \sum_s k_s \times Y_{ce_s} \quad \text{[Mathematical formula 11]}$$

Herein, ks is an important parameter which relates to the scale s.

Referring again to FIG. 5, in operation S520, a block-wise statistics operation which relates to the input image is performed.

Next, in operation S530, uniformity compensation is performed.

In an exemplary embodiment, the local contrast enhancement method to be performed is nonuniform in time and space. This is because the anticipated curve regarding each CLAHE block is estimated from the block statistics operation performed in operation S520. The block statistics change sequentially in space and time. The nonuniformity may cause time flicker and spatial distortion. Therefore, in order to prevent time flicker, it is possible to use a local contrast enhancement curve for temporal smoothing, and it is also possible to use a local contrast enhancement curve for spatial smoothing and for obtaining a modified CLAHE block arrangement.

First, in order to prevent a time flicker, a smooth local contrast enhancement curve is used. When the location of an object is changed quickly in a video, a time flicker appears. This suddenly changes the local histogram and causes time flicker. In order to prevent such a quick change of histogram, a smooth local contrast enhancement curve is used instead of the current curve gcd which relates to each CLAHE block.

In order to calculate the local contrast enhancement curve, an Alpha filter as expressed below is used:

$$\hat{g}_{ce}(t) = \hat{g}_{ce}(t-1) + \alpha_{mem} \times (g_{ce}(t) - \hat{g}_{ce}(t-1)) \quad \text{[Mathematical formula 12]}$$

Herein, t is the current frame number, and αmem is the memory of the filter.

Most of the actual video includes scene changes, and a scene is rapidly converted. In this regard, the memory parameter αmem of the filter varies based on the scene change probability $P_{SC}$ as expressed in the formula below:

$$\alpha_{mem} = \max(\alpha_n, k_m \times P_{SC}) \quad \text{[Mathematical formula 13]}$$

Herein, αn is a memory of the normal filter, and km is a scene change memory gain parameter.

In order to calculate the scene change probability Psc, the correlation coefficient ρ between the current frame and the previous frame is used as expressed in the formulas below:

$$P_{SC} = \begin{cases} 1 - \max(0, \rho) & \text{if } \max(\sigma(t), \sigma(t-1)) \geq \sigma_{min} \\ 0 & \text{otherwise} \end{cases} \quad \text{[Mathematical formula 14]}$$

$$\rho = \frac{E[(Y(t) - \bar{Y}(t))(Y(t-1) - \bar{Y}(t-1))]}{\sigma(t)\sigma(t-1)} \quad \text{[Mathematical formula 15]}$$

Herein, σ(t) is the average dispersion of the fimbriation brightness luminance of frame t, and σmin is the numerical stability constant.

Second, a method for reducing space distortion is used. Space distortion occurs due to block perspective local processing.

First, in the local contrast enhancement procedure, spatial smoothing of the local contrast enhancement curve having a gaussian filter is performed prior to bilinear interpolation. With respect to another scale, the gaussian filter uses a different support window ds*ds and a different standard dispersion σs.

Next, in operation S540, a spatial block arrangement regarding the multi-scale CLAHE is designed. Since spatial distortion mostly occurs in the block boundary, the block is arranged to minimize the unconformity of the boundary in different scales. To this end, the numbers of rows and lines are determined in different fractions and for all the same scales.

Next, in operation S550, the overall contrast adjustment result Yba and local contrast enhancement result Yce are combined as expressed in the formula below:

$$Y_c = (1 - w_{ce}) \times Y_{ba}(x,y) + w_{ce} \times Y_{ce} \quad \text{[Mathematical formula 16]}$$

Herein, wce is the weighted value of the local contrast enhancement.

Next, the luminance enhancement gain gb is calculated as expressed in the formula below.

$$g_b(x,y) = Y_{ce}/Y_b \quad \text{[Mathematical formula 17]}$$

Because the low frequency element of fimbriation brightness is used to calculate the enhancement, the luminance gain is smooth and does not increase noise.

Next, in operation S560, a luminance enhancement is performed.

In order to enhance the original luminance Y, the gain is calculated as expressed in the formula below:

$$Y_{out}(x,y) = Y(x,y) \times g_b(x,y) \quad \text{[Mathematical formula 18]}$$

Next, a color compensation parameter is calculated.

After adjusting the luminance, the fimbriation element C={Cb; Cr} must be adjusted as expressed in the formula below.

$$C_{out}(x,y) = C(x,y) \times g_c(x,y) \quad \text{[Mathematical formula 19]}$$

Next, in operation S570, color compensation is performed.

In this case, it is possible to perform the color adjustment procedure in such a manner as to prevent a large scale color noise boost in the dark area where luminance increases, and also to preserve the color of the unchanged skin area in order to avoid an unnatural color tint.

To this end, the color gain gc is calculated using the gain gb as expressed in the formula below.

$$g_c = \begin{cases} 1, & \text{if } g_b < 1 \\ 1 + (g_b - 1) \times P_n \times P_s, & \text{otherwise} \end{cases} \quad \text{[Mathematical formula 20]}$$

Herein, Pn is the color noise probability, and Ps is the probability of the pixel to be a part of the skin area.

First, the color gain which relates to the pixels having the probability Pn with respect to inclusion of the fimbriation noise is reduced. In addition, Pn is calculated as expressed in the formula below.

$$P_n = \min(1, Y_b \times k_n) \quad \text{[Mathematical formula 21]}$$

Herein, kn is the color noise intensity coefficient.

Secondly, the color gain which relates to the pixels having a high probability Ps to be a part of the skin area is reduced as expressed in the formula below. In addition, Ps with respect to the pixels having fimbriation elements Cb and Cr are calculated.

$$P_s = \min\left(\frac{\max(|Cb - Cb_c|, |Cr - Cr_c|)}{d_m}, 1\right) \quad \text{[Mathematical formula 22]}$$

Herein, {Cbc; Crc} is the center of YCbCr color space, and dm is the size of the skin cluster in the YCbCr color space, where Y refers to a luminance component, Cb refers to a blue-difference chroma component, and Cr refers to a red-difference chroma component.

It is possible to perform software compensation with respect to the photographed image by executing the aforementioned method.

Figure 7:
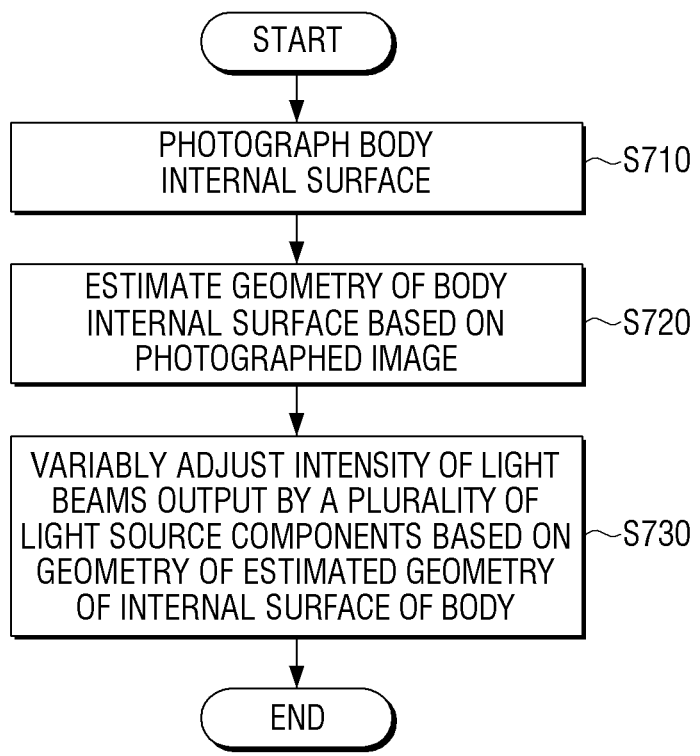
FIG. 7 is a view which illustrates a control method which is executable by using an endoscopic apparatus, in accordance with one or more exemplary embodiments.

FIG. 7 is a view which illustrates a control method which is executable by using an endoscopic apparatus, according to an exemplary embodiment.

In operation S710 of the control method of the endoscopic apparatus illustrated in FIG. 7, the internal surface of the body is photographed. In operation S720, the geometry of the internal surface of the body is estimated.

In this case, it is possible to photograph the internal surface of the body and then estimate the geometry of the internal surface of the body based on the photographed image.

In an alternative exemplary embodiment, it is possible to sense the depth of the internal surface of the body and then estimate the geometry of the internal surface of the body based on the sensed depth.

Next, in operation S730, the intensity of the light beam which is output by a corresponding one of the plurality of light source components is variably adjusted based on the estimated geometry of the internal surface of the body.

Herein, the plurality of light source components may output light beams which cross one another.

In addition, there may be further included an operation of adjusting an output state of at least one of the plurality of light beams which are output by the plurality of light source components, in which case it is possible to adjust at least one of the emission direction and emission extent of the at least one of the plurality of light beams based on the estimated geometry of the internal surface of the body.

In addition, with respect to variably adjusting the intensity of the at least one light beam in operation S730, it is possible to adjust the intensity of each of the plurality of light beams based on the distance between the corresponding one of the plurality of light source components and the internal surface of the body, and/or based on the refraction ratio which relates to the internal surface of the body.

According to the aforementioned exemplary embodiments, it becomes possible to provide illumination which varies dynamically based on the geometry of the internal surface of the body.

In particular, in the aforementioned exemplary embodiments, the illumination adjustment method has been described with respect to potential uses in the endoscopic area, but is not limited thereto, and thus may be used in various industrial areas for providing appropriate illumination. For example, the illumination adjustment method may be used in connection with devices which are applicable to various industrial areas, such as, for example, observing inside without having to disassemble a precision machine, or observing whether or not there is a problem inside a pipe.

Further, the control method of the endoscopic apparatus according to various exemplary embodiments may be embodied as a program and be provided in an endoscopic apparatus.

As an example, it is possible to provide a non-transitory computer readable medium which stores a program which performs a process for variably adjusting an intensity of a light beam output by a corresponding one of a plurality of light source components based on an estimated geometry of an internal surface of a body.

A non-transitory computer readable medium refers to a medium which stores data semi-permanently and which enables reading thereof by an apparatus, such as, for example, a computer. More particularly, the aforementioned various applications or programs may be stored and provided in a non-transitory computer readable medium such as, for example, a hard disk, a Blu-ray disk, a universal serial bus (USB) device, a memory card, ROM, and/or any other suitable medium.

In addition, although a bus is not illustrated in the above-described block diagrams which illustrate an electronic apparatus, communication among each configurative element may be performed via a bus. In addition, a processor, such as, for example, a CPU and/or a microprocessor which performs various aforementioned operations, may be further included in each device.

Although a few exemplary embodiments have been shown and described, it will be appreciated by those skilled in the art that changes may be made with respect to these exemplary embodiments without departing from the principles and spirit of the present inventive concept, the scope of which is defined in the claims and their equivalents.

What is claimed is:

1. An endoscopic apparatus comprising:
  a light source which includes a plurality of light source components which are configured to output light beams which cross one another;
  an estimator which is configured to estimate a geometry of an internal surface of a body; and
  a controller which is configured to control so that an intensity of a light beam output by any one of the plurality of light source components is variably adjusted based on the estimated geometry of the internal surface of the body, and to control so that at least one from among an emission direction and an emission extent of at least one light beam output by one of the plurality of light source components is adjusted based on the estimated geometry of the internal surface of the body.

2. The endoscopic apparatus according to claim 1, further comprising a light adjuster which is configured to adjust an output state of the at least one of a plurality of light beams output by the plurality of light source components,
  wherein the controller is further configured to control the light adjuster to adjust the at least one from among the emission direction and the emission extent of the at least one of the plurality of light beams based on the estimated geometry of the internal surface of the body.

3. The endoscopic apparatus of claim 2, wherein the controller is further configured to control so that the intensity of a first one of the plurality of light beams which is output by a first one of the plurality of light source components is variably adjusted based on the estimated geometry of the internal surface of the body, and
  wherein the controller is further configured to control the light adjuster to adjust the emission direction of a second one of the plurality of light beams which is output by a second one of the plurality of light source components based on the estimated geometry of the internal surface of the body, and to control the light adjuster to adjust the emission extent of a third one of the plurality of light beams which is output by a third one of the plurality of light source components based on the estimated geometry of the internal surface of the body.

4. The endoscopic apparatus according to claim 1, further comprising a photographer which is configured to photograph the internal surface of the body,
  wherein the estimator is further configured to estimate the geometry of the internal surface of the body based on an image which is generated by the photographer.

5. The endoscopic apparatus of claim 4, wherein the controller is further configured to perform a local contrast enhancement with respect to the image generated by the photographer.

6. The endoscopic apparatus of claim 4, wherein the controller is further configured to perform a luminance enhancement with respect to the image generated by the photographer.

7. The endoscopic apparatus of claim 4, wherein the controller is further configured to perform a color compensation with respect to the image generated by the photographer.

8. The endoscopic apparatus according to claim 1, further comprising a depth sensor which is configured to sense a depth of the internal surface of the body,
  wherein the estimator is further configured to estimate the geometry of the internal surface of the body based on the depth sensed by the depth sensor.

9. The endoscopic apparatus according to claim 1, wherein the controller is further configured to adjust an intensity of at least one of the plurality of light beams based on an angle between a normal component with respect to the estimated geometry of the internal surface of the body and a direction of the at least one of the plurality of light beams.

10. An endoscopic method comprising:
  estimating a geometry of an internal surface of a body;
  variably adjusting an intensity of a light beam which is output by one of a plurality of light source components based on the estimated geometry of the internal surface of the body; and
  variably adjusting at least one from among an emission direction and an emission extent of at least one light beam output by one of the plurality of light source components based on the estimated geometry of the internal surface of the body,
  wherein the plurality of light source components are configured to output a respective plurality of light beams which cross one another.

11. The endoscopic method according to claim 10, further comprising:
  adjusting an output state of the at least one of the plurality of light beams output by the plurality of light source components,
  wherein the adjusting the output state of the at least one of the plurality of light beams includes the variably adjusting the at least one from among the emission direction and the emission extent of the at least one of the plurality of light beams based on the estimated geometry of the internal surface of the body.

12. The endoscopic method of claim 11, wherein the variably adjusting the intensity of the light beam includes variably adjusting the intensity of a first one of the plurality of light beams which is output by a first one of the plurality of light source components based on the estimated geometry of the internal surface of the body, and
  wherein the adjusting the output state of the at least one of the plurality of light beams includes adjusting the emission direction of a second one of the plurality of light beams which is output by a second one of the plurality of light source components based on the estimated geometry of the internal surface of the body, and adjusting the emission extent of a third one of the plurality of light beams which is output by a third one of the plurality of light source components based on the estimated geometry of the internal surface of the body.

13. The endoscopic method according to claim 10, further comprising photographing the internal surface of the body,
  wherein the estimating the geometry of the internal surface of the body includes estimating the geometry of the internal surface of the body based on an image which is obtained as a result of the photographing.

14. The endoscopic method of claim 13, further comprising performing a local contrast enhancement with respect to the image which is obtained as the result of the photographing.

15. The endoscopic method of claim 13, further comprising performing a luminance enhancement with respect to the image which is obtained as the result of the photographing.

16. The endoscopic method of claim 13, further comprising performing a color compensation with respect to the image which is obtained as the result of the photographing.

17. The endoscopic method according to claim 10, further comprising sensing a depth of the internal surface of the body,
  wherein the estimating the geometry of the internal surface of the body includes estimating the geometry of the internal surface of the body based on the sensed depth.

18. The endoscopic method according to claim 10, wherein the variably adjusting the intensity of the light beam includes variably adjusting the intensity of the light beam based on at least one of a normal component with respect to the estimated geometry of the internal surface of the body, a direction of the light beam, a distance between the one of the plurality of light source components from which the light beam is output and the internal surface of the body, and a refraction ratio which relates to the internal surface of the body.

19. A non-transitory computer-readable recording medium having stored thereon a program which is executable by a computer for performing an endoscopic method comprising:
  estimating a geometry of an internal surface of a body;
  variably adjusting an intensity of a light beam which is output by one of a plurality of light source components based on the estimated geometry of the internal surface of the body; and
  variably adjusting at least one from among an emission direction and an emission extent of at least one light beam output by one of the plurality of light source components based on the estimated geometry of the internal surface of the body,
  wherein the plurality of light source components are configured to output a respective plurality of light beams which cross one another.

* * * * *